US010023690B2

(12) United States Patent
Mueller-Cristadoro et al.

(10) Patent No.: US 10,023,690 B2
(45) Date of Patent: Jul. 17, 2018

(54) HYPERBRANCHED PHOSPHORIC ACID ESTERS

(71) Applicant: BASF SE, Ludwigshafen (DE)

(72) Inventors: Anna Mueller-Cristadoro, Waldems (DE); Frank Pirrung, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 157 days.

(21) Appl. No.: 14/426,015

(22) PCT Filed: Sep. 4, 2013

(86) PCT No.: PCT/EP2013/068287
§ 371 (c)(1),
(2) Date: Mar. 4, 2015

(87) PCT Pub. No.: WO2014/044529
PCT Pub. Date: Mar. 27, 2014

(65) Prior Publication Data
US 2015/0210804 A1    Jul. 30, 2015

Related U.S. Application Data

(60) Provisional application No. 61/703,288, filed on Sep. 20, 2012.

(30) Foreign Application Priority Data

Sep. 20, 2012 (EP) .................... 12185224

(51) Int. Cl.
C07F 9/09 (2006.01)
C08G 64/42 (2006.01)
C08G 65/26 (2006.01)
C08G 65/327 (2006.01)
C08G 65/48 (2006.01)
C08K 5/521 (2006.01)
C09D 5/00 (2006.01)
C09D 7/45 (2018.01)
C09D 7/65 (2018.01)
C09D 11/03 (2014.01)
C09D 11/326 (2014.01)
C09D 17/00 (2006.01)

(52) U.S. Cl.
CPC ............. C08G 64/42 (2013.01); C07F 9/091 (2013.01); C08G 65/2603 (2013.01); C08G 65/327 (2013.01); C08G 65/48 (2013.01); C08K 5/521 (2013.01); C09D 5/00 (2013.01); C09D 7/45 (2018.01); C09D 7/65 (2018.01); C09D 11/03 (2013.01); C09D 11/326 (2013.01); C09D 17/00 (2013.01); C08G 2650/30 (2013.01); C08G 2650/52 (2013.01)

(58) Field of Classification Search
CPC .... C08G 64/42; C08G 65/48; C08G 2650/30; C08G 65/2603; C08G 65/327; C08G 2650/52; C07F 9/091; C08K 5/521; C09D 7/02; C09D 11/03; C09D 11/326; C09D 17/00; C09D 5/00; C09D 7/125; C09D 7/45; C09D 7/65
See application file for complete search history.

(56) References Cited

U.S. PATENT DOCUMENTS

| 2,965,590 | A | * | 12/1960 | Schumacher | .......... C09D 5/024 524/127 |
| 3,932,532 | A | | 1/1976 | Hunter et al. | |
| 5,202,111 | A | * | 4/1993 | Spaltro | .................... A61K 8/60 424/49 |
| 5,728,796 | A | | 3/1998 | Liao et al. | |
| 7,595,416 | B2 | * | 9/2009 | Pirrung | .................. C08K 5/521 523/160 |
| 2004/0127749 | A1 | * | 7/2004 | Harrison | ............. B01F 17/0021 568/300 |
| 2010/0280165 | A1 | | 11/2010 | Terrenoire et al. | |
| 2014/0171526 | A1 | | 6/2014 | Cristadoro et al. | |

FOREIGN PATENT DOCUMENTS

| CN | 101910207 A | 12/2010 |
| CN | 102633999 A | 8/2012 |
| DE | 10307172 | 5/1958 |
| DE | 4446877 A1 | 7/1996 |
| DE | 19947631 A1 | 6/2000 |
| DE | 19904444 A1 | 8/2000 |
| DE | 10163163 A1 | 7/2003 |
| DE | 10211664 A1 | 10/2003 |
| DE | 10219508 A1 | 11/2003 |

(Continued)

OTHER PUBLICATIONS

Machine English translation of CN 102633999, Wang et al., 8/115/ 2012.*
Bin Zhong, et al, "Novel coatings from soybean oil phosphate ester polyols," JCT, Journal of Coatings Technology, vol. 73, No. 915, XP009098710, Apr. 1, 2001, pp. 53-57.
Yinzhong Guo, et al., "Self-Emulsifiable Soybean Oil Phosphate Ester Polyols for Low-VOC Corrosion Resistant Coatings," JCT Research, vol. 3, No. 4, XP055049639, Jan. 1, 2006, pp. 327-331.
Flora Elvistia Firdaus, "Polymerization of Ethylene Glycol and Soy-epoxide Derived Phosphate Ester for Polyurethane Foam," International Journal of Chemistry, vol. 4, No. 3, XP055050245, May 27, 2012, pp. 98-103.

(Continued)

Primary Examiner — Patrick D Niland
(74) Attorney, Agent, or Firm — Oblon, McClelland, Maier & Neustadt, L.L.P.

(57) ABSTRACT

The present invention is directed to a process for preparing hyperbranched phosphoric acid esters as well as a hyperbranched phosphoric acid ester, its use for dispersing solid substances and in the production of water- and/or solvent-based coatings and paints, printing inks and/or plastics such as unsaturated polyesters, PVC or plastisols and a pigment dispersion comprising the at least one hyperbranched phosphoric acid ester or salt thereof and its use as a component in paints or lacquers.

13 Claims, No Drawings

(56) References Cited

FOREIGN PATENT DOCUMENTS

| | | | |
|---|---|---|---|
| DE | 10240817 A1 | 3/2004 |
| EP | 0141253 A1 | 5/1985 |
| EP | 0417490 A2 | 3/1991 |
| EP | 1036106 | 9/2000 |
| JP | 2004-531363 A | 10/2004 |
| JP | 2007-161928 A | 6/2007 |
| WO | 95/34593 | 12/1995 |
| WO | 97/02304 | 1/1997 |
| WO | 99/16810 | 4/1999 |
| WO | 00/56802 | 9/2000 |
| WO | 01/46296 A1 | 6/2001 |
| WO | 02/057004 A1 | 7/2002 |
| WO | 03/062306 A1 | 7/2003 |
| WO | 03/066702 A1 | 8/2003 |
| WO | 2004/074346 A1 | 9/2004 |
| WO | 2005/007726 A1 | 1/2005 |
| WO | 2005/026234 A1 | 3/2005 |
| WO | 2005/044897 A1 | 5/2005 |
| WO | 2005/075541 A1 | 8/2005 |
| WO | 2005/085261 A1 | 9/2005 |
| WO | 2006/018125 A1 | 2/2006 |
| WO | 2006/087227 A2 | 8/2006 |
| WO | 2006/089940 A1 | 8/2006 |
| WO | 2009/047269 A2 | 4/2009 |
| WO | 2009/101141 A1 | 8/2009 |
| WO | WO 2011/144726 A1 | 11/2011 |

OTHER PUBLICATIONS

Kenta Hagiwara, et al., "Endowed Multi-functionality of Branced Oligosaccharide from Corn Starch by Phosphorylation and Oleylation," J. Appl. Glycosci., vol. 58, XP055050231, Jan. 1, 2011, pp. 71-77.

Zhaoxing Liu, et al., "Cross-Linked PEG via Degradable Phosphate Ester Bond: Synthesis, Water-Swelling, and Application as a Drug Carrier," Biomacromolecules, vol. 12, No. 6, XP055050237, Jun. 13, 2011, pp. 2389-2395.

Zhanguang Huang, et al., "Thermal degradation behavior of hyperbranched polyphosphate acrylate/tri(acryloyloxyethyl) phosphate as an intumescent flame retardant system," Polymer Degradation and Stability, vol. 92, No. 7, XP022133492, Jun. 28, 2007, pp. 1193-1198.

Chaojian Chen, et al., "Photo-responsive, biocompatible polymeric micelles self-assembled from hyperbranched polyphosphate-based polymers," Polymer Chemistry, vol. 2, No. 6, XP055049640, Jan. 1, 2011, 10 pages.

International Search Report dated Oct. 8, 2013 in PCT/EP2013/068287 filed Sep. 4, 2013.

Office Action dated Feb. 29, 2016 in Japanese Patent Application No. 2015-531518 (submitting English translation only).

Office Action dated May 4, 2016 in Chinese Patent Application No. 201380047829.0 (submitting English translation only).

U.S. Appl. No. 14/104,135, filed Dec. 12, 2013, US2014/0171526 A1, Cristadoro, et al.

Office Action dated Feb. 8, 2017, in European Patent Application No. 13759998, filed Sep. 4, 2013.

V. Mannari, "POLY 598—Dispersability of Phosphated Bio-Based Hyperbranched Polyols", The 225$^{th}$ ACS National Meeting, New Orleans, LA, Mar. 23-27, 2003, XP055341322.

J.L. Massingill, et al., "High Performance Low VOC Coatings for 2006", Final Report Seminar, Mar. 9, 2006, XP055341884.

B. Ahn, "Design and Preparation of Plant Oil-Based Polymers and Their Applications", PhD Thesis, Jan. 1, 2011, pp. 1-149, XP055341871.

P.J. Flory, "Molecular Size Distribution in Three Dimensional Polymers. VI. Branched Polymers Containing A-R-B$_{1-1}$ Type Units", J. Am.Chem.Soc., 1952, vol. 74.

A. Sunder, et al., "Controlling the Growth of Polymer Trees: Concepts and Perspectives for Hyperbranched Polymers", Chem. Eur. J., 200. vol. 6, No. 14.

Chen, et al.. "Synthesis of Multihydroxyl Branched Polyethers by Cationic Copolymerization of 3,3-Bis(Hydroxymethyl)Oxetane and 3-Ethyl-3-(Hydroxymethyl)Oxetane", J. Poly. Sci. Part A: Polymer Chemistry, vol. 40, Issue 12, Jun. 15, 2002.

Final Rejection, dated Nov. 27, 2015, Final Resp (3rd).

Final Rejection, dated Nov. 27, 2015, Notice of Appeal (3rd).

Final Rejection, dated Sep. 21, 2016, Appeal due, filed Dec. 21, 2016.

Final Rejection, dated Sep. 21, 2016 Final rejection response due, filed Dec. 21, 2016.

Final Rejection, dated Sep. 21, 2016, Request for continued examination, filed Dec. 21, 2016.

* cited by examiner

HYPERBRANCHED PHOSPHORIC ACID ESTERS

The present invention is directed to a process for preparing hyperbranched phosphoric acid esters as well as a hyperbranched phosphoric acid ester, its use for dispersing solid substances and in the production of water- and/or solvent-based coatings and paints, printing inks and/or plastics such as unsaturated polyesters, PVC or plastisols and a pigment dispersion comprising the at least one hyperbranched phosphoric acid ester or salt thereof and its use as a component in paints or lacquers.

Typically, high mechanical forces are necessary in order to introduce solid substances, such as pigments, in a liquid medium. This depends to a large extent on the solid substance's wettability by the surrounding medium, as well as on the affinity for the respective liquid medium used. In order to reduce these forces, dispersing agents are widely used which facilitate the incorporation of the solid substances in the liquid medium. Common dispersing agents are surface-active agents such as polymers or surfactants of anionic or cationic or non-ionic structure. In relatively low amounts of addition, these agents are either applied directly to the solid substance or added to the liquid medium. By using such a surfactant, the energy required for dispersion is considerably reduced.

Furthermore, it is known that such solid substances, after dispersion, have the tendency to reagglomerate in the liquid medium, which nullifies the initially induced dispersing energy and causes severe problems. This phenomenon can be explained by inter alia London/van der Waals' forces by which the solid substances are mutually attracted. In order to reduce these attractive forces, adsorption layers in the form of such dispersing agents are provided on the solid substance's surface.

However, during and after dispersion an interaction of the surrounding liquid medium with the solid substance may lead to a desorption of the respective dispersing agent used so that a high amount of said dispersing agent is exchanged against the surrounding liquid medium. However, in most cases this surrounding liquid medium is incapable of building up a stable adsorption layer so that the entire system flocculates. This is evidenced by inter alia a viscosity increase in the liquid system, loss of gloss, color shifts in paints and coatings, insufficient development of color strength in pigmented plastics and lacquers, as well as a decrease of the mechanical strength in reinforced plastics.

In the art, several attempts for improving the dispersing properties of surfactants and polymers for pigments, fillers and extenders have been proposed. For instance, European Patent EP 0417 490 A2 describes phosphoric acid esters and their salts corresponding to the formula $(HO)_3$-n-PO—(OR)n, wherein R is an aliphatic, cycloaliphatic and/or aromatic residue containing at least one ether oxygen (—O—) and at least one carboxylic acid ester group (—COO—) and/or urethane group (—NHCOO—) without Zerewitinoff hydrogen. As an example, a compound of formula Alkyl-[O(CH$_2$)x]z-[O—C=O(CH$_2$)x]y-O—P=O(OH)$_2$ is disclosed.

WO 95/34593 A1 describes a dispersant obtainable by reacting a polyethylene glycol with a hydroxycarboxylic acid and/or with an alkylene oxide to form a polymeric diol and phosphating the diol. WO 2005/085261 A1 describes linear phosphoric acid esters having both phosphoric and carboxylic acid groups by reacting a mono-, di-, tri- or polyhydroxy di-, tri- or multi-carboxylic acid residue with mono-OH functional polymeric chains. WO 02/057004 A1 describes dendritic structures, comprising a core, a number of branching generations and an external surface composed of functional reactive groups selected from the groups of OH, NCO, carboxyl and amines, which are reacted with a group R—X, R being a spacer and X a pigment affinic group based on N-containing groups, COOH groups, phosphoric esters and sulphonic ester moieties.

However, the preparation of said dispersing agents is challenging. For instance, the preparation of such dispersing agents is typically achieved in a time-consuming multistep reaction. Furthermore, such multistep reaction does not allow an easy modification of the dispersing agent in order to adapt the functionality of the dispersing agent to the requirements of the respective application. In addition thereto, such multistep reaction requires the use of high amounts of chemicals and solvents for the preparation and the subsequent purification of the dispersing agent and is thus highly cost-consuming.

Thus, there is a need in the art for providing a process which avoids the foregoing disadvantages and especially allows for the preparation of dispersing agents imparting very well mechanical properties to a resulting end product while its optical properties are kept on a high level.

Accordingly, it is an object of the present invention to provide a time-efficient process for preparing a dispersing agent. Furthermore, it is an object of the present invention that the degree of functionality of the dispersing agent can be easily modified in accordance with the requirements of the respective end application. In addition thereto, it is an object of the present invention to provide a process in which the total amount of chemicals and solvents required for the preparation and the subsequent purification is reduced and, thus, also reduces the costs for its preparation. It is a further object of the present invention to provide a process for preparing a dispersing agent, wherein the resulting end product comprising said dispersing agent has very well balanced rheology (expressed by a low viscosity) and solubility behavior in aprotic media while the optical properties such as haze as well as the gloss of the resulting end product are kept on a high level. Further objects can be gathered from the following description of the invention.

This and other objects are solved by the subject-matter of the present invention. According to a first aspect of the present invention, a process for preparing hyperbranched phosphoric acid esters is provided, wherein the process comprises at least the steps of:
  a) providing at least one hyperbranched polymer comprising terminal primary hydroxyl groups and/or secondary hydroxyl groups,
  b) providing at least one phosphoric acid ester-forming compound,
  c) reacting the at least one hyperbranched polymer of step a) with the at least one phosphoric acid ester-forming compound of step b) such as to obtain the hyperbranched phosphoric acid ester.

The inventors surprisingly found that the foregoing process for preparing hyperbranched phosphoric acid esters according to the present invention avoids the use of time- and cost-consuming multistep reactions and leads to resulting end products having very well balanced mechanical and optical properties. More precisely, the inventors found that the properties of a dispersing agent being obtained by said process can be easily modified by reacting a hyperbranched polymer with a phosphoric acid ester-forming compound.

It should be understood that for the purposes of the present invention, the following terms have the following meanings:

The term "hyperbranched" in the meaning of the present invention refers to the degree of branching (DB), which is to say branched polymers can be characterized by their degree of branching (DB). This degree of branching DB is defined as $$DB\ (\%)=(T+Z)/(T+Z+L)\times 100,\ \text{where}$$

T is the average number of terminally attached monomer units, Z is the average number of monomer units which form branches, and L is the average number of linearly attached monomer units. Highly branched polymers in the context of this invention have a degree of branching DB of 10% to 100%, preferably 10% to 90%, and more preferably 10% to 80%. Dendrimers generally have a degree of branching DB of at least 99%, more particularly 99.9% to 100%. Hyperbranched polymers have a degree of branching DB of 10% to 95%, preferably 25% to 90%, and more preferably 30% to 80%.

In the context of the present invention, it is possible in principle to use not only the structurally and molecularly uniform dendrimers but also the molecularly and structurally nonuniform hyperbranched polymers.

The term "hyperbranched polymer" for the purposes of this invention are noncrosslinked macromolecules containing hydroxyl, ester, amid, ether, carbonate, etheramino, amino, imide, urethane, urea, or carbamoyl chloride groups and also their hybrid forms such as esteramid, etheramid, etherester, polyesteramines, ureaurethane groups etc. within the polymer and/or as terminal end groups, said macromolecules having both structural and molecular nonuniformity. On the one hand, starting from a central molecule, they can have a construction analogous to that of dendrimers, but with the chain length of the branches being nonuniform. On the other hand they can also be linear in construction, with functional side groups, or else may have both linear and branched moieties, as a combination of the two extremes. On the definition of dendrimeric and hyper-branched polymers see also P. J. Flory, J. Am. Chem. Soc. 1952, 74, 2718 and H. Frey et al., Chem. Eur. J. 2000, 6, No. 14, 2499.

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

According to another aspect of the present invention, a hyperbranched phosphoric acid ester or salt thereof is provided, the hyperbranched phosphoric acid ester or salt thereof comprising
  i) at least one hyperbranched polymer, wherein the at least one hyperbranched polymer comprises terminal primary hydroxyl groups and/or secondary hydroxyl groups, and
  ii) phosphoric ester moieties which have been formed with the terminal primary hydroxyl groups and/or secondary hydroxyl groups of the at least one hyperbranched polymer.

According to a further aspect, the present invention refers to the use of such hyperbranched phosphoric acid ester for dispersing solid substances. According to another aspect, the present invention refers to the use of such hyperbranched phosphoric acid ester in the production of water- and/or solvent-based coatings and paints, printing inks and/or plastics such as unsaturated polyesters, PVC or plastisols. According to still further aspect, the present invention refers to a pigment dispersion, comprising a) at least one pigment, b) the at least one hyperbranched phosphoric acid ester or salt thereof, and c) water or an organic solvent or an inert carrier like a plasticizer. It is preferred that the at least one pigment is selected from organic and/or inorganic pigments. According to an even further aspect, the present invention refers to the use of the pigment dispersion as a component in paints or lacquers.

According to one embodiment of the inventive process, the at least one hyperbranched polymer is selected from the group comprising polycarbonates, polyethers, polyetheramines, polyesters, polyurethanes, polyurea, polyimide, polyamide, polyesteramide and mixtures thereof.

According to another embodiment of the inventive process, the at least one hyperbranched polymer is a polyether, e.g. a homo- or copolymer of tris-2-hydroxyethylisocyanurate, a polyetheramine or a polycarbonate.

According to yet another embodiment of the inventive process, the at least one phosphoric acid ester-forming compound is polyphosphoric acid and/or $P_2O_5$.

According to one embodiment of the inventive process, the at least one phosphoric acid ester-forming compound of step b) is provided in an amount such that the degree of functionalization in the hyperbranched phosphoric acid ester is in the range of from 0.5 to 100%, based on the total amount of terminal primary hydroxyl groups and/or secondary hydroxyl groups in the polymer of step a).

According to another embodiment of the inventive process, the at least one phosphoric acid ester-forming compound of step b) is provided in an amount such that the degree of functionalization in the hyperbranched phosphoric acid ester is in the range of from 0.5 to 50%, based on the total amount of terminal primary hydroxyl groups and/or secondary hydroxyl groups in the polymer of step a).

According to yet another embodiment of the inventive process, the at least one phosphoric acid ester-forming compound of step b) is provided in an amount such that the degree of functionalization of the hyperbranched phosphoric acid ester is in the range of from 0.5 to 25%, based on the total amount of terminal primary hydroxyl groups and/or secondary hydroxyl groups in the polymer of step a).

According to one embodiment of the inventive process, reacting step c) is carried out at a temperature of from 20° C. to 200° C.

According to another embodiment of the inventive process, reacting step c) is carried out in an inert atmosphere, like nitrogen or argon.

According to yet another embodiment of the inventive process, the process further comprises step d) of forming a phosphate salt by neutralizing the hyperbranched phosphoric acid ester obtained in step c) with an amine or inorganic base like alkali hydroxide.

As set out above, the inventive process for preparing hyperbranched phosphoric acid esters comprises the steps a), b) and c). In the following, it is referred to further details of the present invention and especially the foregoing steps of the inventive process for preparing hyperbranched phosphoric acid esters.

It is one requirement of the present invention that at least one hyperbranched polymer comprising terminal primary hydroxyl groups and/or secondary hydroxyl groups is provided.

The expression "at least one" hyperbranched polymer means that one or more kinds of hyperbranched polymers may be provided in the process of the present invention.

In particular, the at least one hyperbranched polymer is a three-dimensional, highly branched oligomeric or polymeric molecules. The at least one hyperbranched polymer provided in accordance with the present invention comprise a core, a number of branching generations and an external surface composed of functional, reactive groups, i.e. terminal primary hydroxyl groups and/or secondary hydroxyl groups. A branching generation is composed of structural units that are bound radially to the core or to the structural units of a previous generation and which extends outwards. The structural units have at least two monofunctional groups and/or at least one monofunctional group and one multifunctional group. The term multifunctional is understood as having a functionality of 2 or higher. To each functionality, a new structural unit may be linked, a higher branching generation being produced as a result. The structural units may either be the same (they are repeated, therefore) for each successive generation, or they may be different. The at least one hyperbranched polymer can be characterized, inter alia, on the basis of a degree of branchings. The term degree of branching of a hyperbranched polymer of a particular generation is understood, here and hereinafter, as the ratio between the number of branching present and the maximum possible number of branchings in a completely branched hyperbranched polymer of the same generation. The term "functional end groups of a hyperbranched polymer" refers to those reactive groups which form part of the external surface. The branchings may occur with greater or lesser regularity. Whilst it is possible, in the hyperbranched polymer which can be used within the scope of the invention, for the branchings at the external surface of the hyperbranched polymer all to be of the same generation, it is also possible for the branchings at the surface to be of different generations. The latter may be the case, for example, if the synthesis of the at least one hyperbranched polymer proceeds in a less controlled manner.

The wording "at least one hyperbranched polymer" in the meaning of the present invention also refers to hyperbranched polymers having defects in the branching structure, hyperbranched polymers having an incomplete degree of branching, asymmetrically branched hyperbranched polymers, star polymers, highly branched polymers, highly branched copolymers and/or block copolymers of highly branched and not highly branched polymers.

In principle, all hyperbranched polymers having functional end groups can be considered for use according to the invention.

It is further appreciated that the at least one hyperbranched polymer comprises a plurality of terminal primary hydroxyl groups and/or secondary hydroxyl groups. The number of terminal primary hydroxyl groups and/or secondary hydroxyl groups of a hyperbranched polymer according to the invention generally varies according to the type and generation of the hyperbranched polymer used. The absolute number of terminal primary hydroxyl groups and/or secondary hydroxyl groups per hyperbranched polymer molecule is at least 4, but preferably it is higher, such as at least 8.

According to one embodiment of the present invention, the at least one hyperbranched polymer is selected from the group comprising polycarbonates, polyethers, polyetheramines, polyesters, polyurethanes, polyurea, polyimide, polyamide, polyesteramide and mixtures thereof.

For example, the at least one hyperbranched polymer is a polyether, preferably a polyether prepared from homo- or copolymers of tris-2-hydroxyethylisocyanurate (THEIC). Alternatively, the at least one hyperbranched polymer is a polycarbonate. In one embodiment of the present invention, the at least one hyperbranched polymer is a polyetheramine.

Hyperbranched polymers that may be suitable in the present invention are described in e.g. WO 2009/101141 A1, WO 2005/026234 A1. The preparation of highly branched polymers is also described in the following documents: WO-A 2005/026234 (highly branched and especially hyperbranched polycarbonates); WO-A 01/46296, DE-A 10163163, DE-A 10219508 and DE-A 10240817 (hyperbranched polyesters); WO-A 09/101,141, WO-A 03/062306, WO-A 00/56802, DE-A 10211664 and DE-A 19947631 (hyperbranched polyethers); WO 2004/074346, U.S. Pat. No. 3,932,532, EP 141253, DE 4446877, U.S. Pat. No. 5,728,796, DE 199 47 631, WO 00/56802, DE 102 11 664, DE 103 07 172 and Chen et. al, J. Poly. Sci. Part A: Polym. Chem. 2002, 40, 199 (polyethers); WO-A 06/087227 (hyperbranched polymers containing nitrogen atom, especially polyurethanes, polyureas, polyamides, poly(esteramides), poly(esteramines)); WO-A 97/02304 and DE-A 19904444 (hyperbranched polyurethanes and hyperbranched poly(ureaurethanes)); WO-A 03/066702, WO-A 05/044897 and WO-A 05/075541 (hyperbranched polyureas); WO-A 05/007726 (hyperbranched, amino-containing polymers, especially poly(esteramines)); WO-A 99/16810 and EP-A 1036106 (hyperbranched poly(esterimides)); WO-A 06/018125 (hyperbranched polyamides); WO-A 06/089940 (hyperbranched poly(estercarbonates)) and WO 2009/047269A2 (highly branched polyetheramine polyols). These documents disclose processes for the preparation of hyperbranched polymers, which are incorporated herein by reference.

One further requirement of the present invention is that at least one phosphoric acid ester-forming compound is provided.

The expression "at least one" phosphoric acid ester-forming compound in the meaning of the present invention means that one or more kinds of phosphoric acid ester-forming compounds may be provided in the process of the present invention.

In particular, it should be noted that each phosphoric acid ester-forming compound may be employed in the inventive process which is suitable for reacting with the terminal primary hydroxyl groups and/or secondary hydroxyl groups of the at least one hyperbranched polymer under the formation of phosphoric acid esters.

According to one embodiment of the present invention, the at least one phosphoric acid ester-forming compound is polyphosphoric acid and/or phosphorus pentoxide. For example, the at least one phosphoric acid ester-forming compound is polyphosphoric acid.

In general, the polyphosphoric acid is of the general formula $H_{(n+2)}P_nO_{(3n+1)}$ is preferred that the polyphosphoric acid has an apparent monomeric $H_3PO_4$ concentration of at least 100%, preferably of at least 105% and most preferably of at least 110%, based on the total weight of the polyphosphoric acid. For example, the polyphosphoric acid has an apparent monomeric $H_3PO_4$ concentration of between 110 and 118%, e.g. about 115%, based on the total weight of the polyphosphoric acid.

It is appreciated that the at least one phosphoric acid ester-forming compound is provided in an amount such that the degree of functionalization in the hyperbranched phosphoric acid ester can be modified in accordance with the requirements of the respective application.

Preferably, the at least one hyperbranched polymer is modified with the at least one phosphoric acid ester-forming compound such that at least 0.5% of the functional end groups of the at least one hyperbranched polymer, i.e. the terminal primary hydroxyl groups and/or terminal secondary hydroxyl groups, are provided with a phosphoric acid ester group, wherein the percentage is based on the total amount of terminal primary hydroxyl groups and/or secondary hydroxyl groups in the at least one hyperbranched polymer.

According to one embodiment of the present invention, the at least one phosphoric acid ester-forming compound is provided in an amount such that the degree of functionalization in the obtained hyperbranched phosphoric acid ester is in the range of from 0.5 to 100%, based on the total amount of terminal primary hydroxyl groups and/or secondary hydroxyl groups in the at least one hyperbranched polymer.

For example, the at least one phosphoric acid ester-forming compound is provided in an amount such that the degree of functionalization in the obtained hyperbranched phosphoric acid ester is in the range of from 0.5 to 50%, based on the total amount of terminal primary hydroxyl groups and/or secondary hydroxyl groups in the at least one hyperbranched polymer. Alternatively, the at least one phosphoric acid ester-forming compound is provided in an amount such that the degree of functionalization in the obtained hyperbranched phosphoric acid ester is in the range of from 0.5 to 25%, based on the total amount of terminal primary hydroxyl groups and/or secondary hydroxyl groups in the at least one hyperbranched polymer.

Additionally or alternatively, it is appreciated that the at least one phosphoric acid ester-forming compound is provided in amount of at least 0.5 Mol $H_{(n+2)}P_nO_{(3n+1)}$ per 3 Mol of terminal primary hydroxyl groups and/or secondary hydroxyl groups in the at least one hyperbranched polymer, preferably in amount of from 0.5 to 1.5 Mol $H_{(n+2)}P_nO_{(3n+1)}$ per 3 Mol of terminal primary hydroxyl groups and/or secondary hydroxyl groups in the at least one hyperbranched polymer. For example, the at least one phosphoric acid ester-forming compound is provided in amount of 1 Mol $H_{(n+2)}P_nO_{(3n+1)}$ per 3 Mol of terminal primary hydroxyl groups and/or secondary hydroxyl groups in the at least one hyperbranched polymer.

According to step c) of the present process, the at least one hyperbranched polymer is reacted with the at least one phosphoric acid ester-forming compound such as to obtain the hyperbranched phosphoric acid ester.

The reacting of step c) is preferably performed under mixing. In the process of the present invention, the at least one hyperbranched polymer is mixed with the at least one phosphoric acid ester-forming compound by any conventional mixing means known to the skilled person.

In one embodiment of the present invention, the at least one phosphoric acid ester-forming compound is added to the at least one hyperbranched polymer. For example, the at least one phosphoric acid ester-forming compound is added to a melt of the at least one hyperbranched polymer.

It is appreciated that the at least one phosphoric acid ester-forming compound is preferably added drop-wise to the at least one hyperbranched polymer. For example, the at least one phosphoric acid ester-forming compound is added drop-wise to a melt of the at least one hyperbranched polymer.

The addition of the at least one phosphoric acid ester-forming compound to the at least one hyperbranched polymer is not critical as long as the obtained mixture is thoroughly mixed. Accordingly, said addition may be carried out at once or in several portions. If the addition of the at least one phosphoric acid ester-forming compound to the at least one hyperbranched polymer is carried out in several portions, the portions may comprise equal amounts of the at least one phosphoric acid ester-forming compound. Alternatively, said portions may comprise unequal amounts of the at least one phosphoric acid ester-forming compound.

In one embodiment of the present invention, reacting step c) takes place without using solvents. If reacting step c) takes place without using solvents, the at least one phosphoric acid ester-forming compound is preferably added to a melt of the at least one hyperbranched polymer.

Accordingly, reacting step c) is carried out at a temperature of from 20 to 200° C. For example, reacting step c) is carried out at a temperature of from 40° C. to 150° C. or 50° C. to 120° C.

Additionally or alternatively, the at least one phosphoric acid ester-forming compound is added to a melt of the at least one hyperbranched polymer.

If the at least one phosphoric acid ester-forming compound is added to a melt of the at least one hyperbranched polymer, the temperature of the at least one phosphoric acid ester-forming compound is preferably adjusted such that its temperature is about equal to the temperature of the at least one hyperbranched polymer.

For the purposes of the present invention, the temperature is considered as being equal if the temperatures of the at least one phosphoric acid ester-forming compound and the melt of the at least one hyperbranched polymer do not differ by more than 20° C., preferably by not more than 15° C. and most preferably by not more than 10° C. For example, the temperatures of the at least one phosphoric acid ester-forming compound and the melt of the at least one hyperbranched polymer do not differ by more than 5° C.

Alternatively, reacting step c) can be carried out in the presence of solvents or solvent mixtures, preferably inert solvents like toluene or xylene. It is appreciated that the solvents or solvent mixtures are preferably dried before use, i.e. before reacting step c) is carried out. Preferably, the solvents or solvent mixtures has a water content of below 0.1 Vol.-%, preferably of below 0.05 Vol.-%, more preferably of below 0.01 Vol.-% and most preferably of below 0.005 Vol.-%, based on the total volume of the solvent or solvent mixture. The presence of solvents during reacting step c) is advantageous if the subsequent use of the hyperbranched phosphoric acid esters obtained in the inventive process is preferably formulated in a solvent.

According to one embodiment of the present invention, reacting step c) is carried out in an inert atmosphere. For example, reacting step c) is carried out under nitrogen or argon, preferably nitrogen.

In one embodiment of the present invention, reacting step c) is carried out in the absence of a catalyst. Alternatively, reacting step c) is carried out in the presence of at least one suitable catalyst, e.g. sulphuric acid.

In one embodiment of the present invention, the process further comprises step d) of forming a phosphate salt by neutralizing the hyperbranched phosphoric acid ester obtained in step c) with an amine or inorganic base like alkali hydroxide such that a neutralized hyperbranched phosphoric acid ester is obtained.

If the inventive process further comprises step d) of forming a phosphate salt by neutralizing the obtained hyperbranched phosphoric acid ester, the neutralizing is preferably carried out by contacting the obtained hyperbranched phosphoric acid ester with an inorganic base like alkali hydroxide, e.g. sodium hydroxide and/or potassium hydroxide.

It is appreciated that step d) of forming a phosphate salt by neutralizing the obtained hyperbranched phosphoric acid ester may be carried out during and/or after reacting step c).

In one embodiment of the present invention, step d) of forming a phosphate salt by neutralizing the obtained hyperbranched phosphoric acid ester is carried out during reacting step c). If neutralizing step d) is carried out during reacting step c), the phosphate salt of the hyperbranched phosphoric acid ester is preferably formed in situ.

For example, the hyperbranched phosphoric acid ester obtained in step c) is modified such that at least 30% of the available functional end groups of the hyperbranched phosphoric acid ester, i.e. the terminal primary hydroxyl groups and/or secondary hydroxyl groups, are neutralized, wherein the percentage is based on the total available amount of terminal primary hydroxyl groups and/or secondary hydroxyl groups in the hyperbranched phosphoric acid ester obtained in step c).

In one embodiment of the present invention, the hyperbranched phosphoric acid ester obtained in step c) is modified such that at least 35%, preferably at least 40%, more preferably at least 45% and most preferably at least 50% of the available functional end groups of the hyperbranched phosphoric acid ester, i.e. the terminal primary hydroxyl groups and/or secondary hydroxyl groups, are neutralized, wherein the percentage is based on the total available amount of terminal primary hydroxyl groups and/or secondary hydroxyl groups in the hyperbranched phosphoric acid ester obtained in step c).

One advantage of the inventive process is its economy. In particular, the preparation of the hyperbranched phosphoric acid ester and the salts thereof can be easily conducted in a time- and cost-efficient one-step reaction, which has technical and economic advantages.

In view of the very good results of the process for preparing hyperbranched phosphoric acid esters as defined above, a further aspect of the present invention refers to a hyperbranched phosphoric acid ester or salt thereof. Such hyperbranched phosphoric acid ester preferably comprises a core, a number of branching generations and an external surface composed of terminal primary hydroxyl groups and/or secondary hydroxyl groups.

Accordingly, the inventive hyperbranched phosphoric acid ester or salt thereof comprises, preferably consists of,
i) at least one hyperbranched polymer, wherein the at least one hyperbranched polymer comprises terminal primary hydroxyl groups and/or secondary hydroxyl groups, and
ii) phosphoric ester moieties which have been formed with the terminal primary hydroxyl groups and/or secondary hydroxyl groups of the at least one hyperbranched polymer.

With regard to the definition of the at least one hyperbranched polymer, the hyperbranched phosphoric acid ester and the salts thereof, and preferred embodiments thereof, reference is made to the comments provided above.

In one embodiment of the present invention, between 0.5 and 100%, preferably between 0.5 and 50% and most preferably between 0.5 and 25% of the total amount of terminal primary hydroxyl groups and/or secondary hydroxyl groups of the at least one hyperbranched polymer comprise phosphoric ester moieties.

It is appreciated that the inventive hyperbranched phosphoric acid ester or salts thereof is free of (chain extender) linking chains located at the external surface of the at least one hyperbranched polymer. Preferably, the hyperbranched phosphoric acid ester or salts thereof is free of (chain extender) linking chains located between the terminal primary hydroxyl groups and/or secondary hydroxyl groups of the at least one hyperbranched polymer and the phosphoric ester moieties.

The term "(chain extender) linking chains" in the meaning of the present invention refers to groups suitable for connecting terminal primary hydroxyl groups and/or secondary hydroxyl groups of the at least one hyperbranched polymer and phosphoric ester moieties. That is to say, the inventive hyperbranched phosphoric acid ester or salts thereof is free of (chain extender) linking chains having at least 2 atoms in the chain and are based on dicarboxylic acids, diols, diamines, hydroxycarboxylic acids, hydroxyamines or amino-carboxylic acids.

Additionally or alternatively, the inventive hyperbranched phosphoric acid ester or salts thereof is free of carboxylic acid ester groups and/or amide groups located at the external surface of the at least one hyperbranched polymer. Preferably, the hyperbranched phosphoric acid ester or salts thereof is free of carboxylic acid ester groups and/or amide groups located between the terminal primary hydroxyl groups and/or secondary hydroxyl groups of the at least one hyperbranched polymer and the phosphoric ester moieties.

According to one embodiment of the present invention, the inventive hyperbranched phosphoric acid ester or salt thereof is preferably obtainable by the process of the present invention.

The obtained hyperbranched phosphoric acid ester may find application as dispersing agent. Accordingly, a further aspect of the present invention refers to the use of the hyperbranched phosphoric acid ester for dispersing solid substances such as pigments (e.g. $TiO_2$, $Fe_2O_3$, carbon black etc.) and/or fillers (e.g. calcium carbonate, talc). The obtained hyperbranched phosphoric acid ester may be furthermore used in the production of water- and/or solvent-based coatings and paints. The obtained hyperbranched phosphoric acid ester may be further used in the production of printing inks and/or plastics such as unsaturated polyesters, PVC or plastisols.

It is preferred that the hyperbranched phosphoric acid ester may be used in combination with other dispersing agents and/or suitable additives. For example, the hyperbranched phosphoric acid ester of the present invention may be used in pure form or in form of a solution, e.g. in water or organic solvent, with a reactive monomer such as 1,4-butanediol diacrylate, 1,6-hexanediol diacrylate, (ethoxylated) neopentylglycol diacrylate, ethoxylated bisphenol A diacrylate, (ethoxylated) trimethylolpropane triacrylate, (ethoxylated) pentaerythritol triacrylate, propoxylated glyceryl triacrylate, di-trimethylolpropane tetraacrylate, dipentaerythritol pentaacrylate, polyethylene or polypropylene glycol diacrylate (and corresponding methacrylates of the above), polyethylene glycol divinylether; or with a non-volatile carrier such as a plasticizer like polyglycol, dibasic esters, fatty acids and oils (e.g. mineral oil), fatty esters, phthalates, benzoic esters, DINCH and the like.

It is to be understood that the advantageous embodiments described above with respect to the inventive process for preparing hyperbranched phosphoric acid esters also can be used for preparing or defining the inventive hyperbranched phosphoric acid ester and its uses. In other words, the preferred embodiments described above and any combinations of these embodiments can also be applied to the inventive hyperbranched phosphoric acid ester and its uses.

In a further aspect, the present invention relates to a pigment dispersion, comprising
 a) at least one pigment (hereinafter also being referred to as pigment (A)),
 b) the at least one hyperbranched phosphoric acid ester or salt thereof obtainable by the process of the present invention, and
 c) water or an organic solvent or an inert carrier like a plasticizer.

The at least one pigment is preferably present in particulate form, i.e., in the form of particles. The at least one pigment can be selected from crude pigments, i.e., untreated as-synthesized pigments. The particles of at least one pigment may be regular or irregular in shape in that, for example, the particles may have a spherical or substantially spherical shape or a needle (acicular) shape.

In one embodiment of the present invention, the at least one pigment is of spherical or substantially spherical shape, i.e., the ratio of the longest diameter to the smallest diameter is in the range from 1.0 to 2.0, preferably up to 1.5.

In one embodiment of the present invention, the at least one pigment has an average particle diameter $d_{50}$ in the range of from 20 nm to 50 µm, preferably in the range from 50 nm to 20 µm and more preferably to a maximum of 5 µm, measured, e.g., by Coulter counter or with a Hegman gauge.

The at least one pigment (A) being part of the inventive pigment dispersion is preferably an insoluble, finely dispersed, organic and/or inorganic colorant, preferably inorganic colorant, as per the definition in German standard specification DIN 55944.

Representative examples of organic pigments are monoazo pigments, such as C.I. Pigment Brown 25; C.I. Pigment Orange 5, 13, 36 and 67; C.I. Pigment Red 1, 2, 3, 5, 8, 9, 12, 17, 22, 23, 31, 48:1, 48:2, 48:3, 48:4, 49, 49:1, 52:1, 52:2, 53, 53:1, 53:3, 57:1, 63, 112, 146, 170, 184, 210, 245 and 251; C.I. Pigment Yellow 1, 3, 73, 74, 65, 97, 151 and 183; disazo pigments, such as C.I. Pigment Orange 16, 34 and 44; C.I. Pigment Red 144, 166, 214 and 242; C.I. Pigment Yellow 12, 13, 14, 16, 17, 81, 83, 106, 113, 126, 127, 155, 174, 176 and 188; anthanthrone pigments, such as C.I. Pigment Red 168 (C.I. Vat Orange 3); anthraquinone pigments, such as C.I. Pigment Yellow 147 and 177; C.I. Pigment Violet 31; anthraquinone pigments, such as C.I. Pigment Yellow 147 and 177; C.I. Pigment Violet 31; anthrapyrimidine pigments: C.I. Pigment Yellow 108 (C.I. Vat Yellow 20); quinacridone pigments, such as C.I. Pigment Red 122, 202 and 206; C.I. Pigment Violet 19; quinophthalone pigments, such as C.I. Pigment Yellow 138; dioxazine pigments, such as C.I. Pigment Violet 23 and 37; flavanthrone pigments, such as C.I. Pigment Yellow 24 (C.I. Vat Yellow 1); indanthrone pigments, such as C.I. Pigment Blue 60 (C.I. Vat Blue 4) and 64 (C.I. Vat Blue 6); isoindoline pigments, such as C.I. Pigment Orange 69; C.I. Pigment Red 260; C.I. Pigment Yellow 139 and 185; isoindolinone pigments, such as C.I. Pigment Orange 61; C.I. Pigment Red 257 and 260; C.I. Pigment Yellow 109, 110, 173 and 185; isoviolanthrone pigments, such as C.I. Pigment Violet 31 (C.I. Vat Violet 1); metal complex pigments, such as C.I. Pigment Yellow 117, 150 and 153; C.I. Pigment Green 8; perinone pigments, such as C.I. Pigment Orange 43 (C.I. Vat Orange 7); C.I. Pigment Red 194 (C.I. Vat Red 15); perylene pigments, such as C.I. Pigment Black 31 and 32; C.I. Pigment Red 123, 149, 178, 179 (C.I. Vat Red 23), 190 (C.I. Vat Red 29) and 224; C.I. Pigment Violet 29; phthalocyanine pigments, such as C.I. Pigment Blue 15, 15:1, 15:2, 15:3, 15:4, 15:6 and 16; C.I. Pigment Green 7 and 36; pyranthrone pigments, such as C.I. Pigment Orange 51; C.I. Pigment Red 216 (C.I. Vat Orange 4); thioindigo pigments, such as C.I. Pigment Red 88 and 181 (C.I. Vat Red 1); C.I. Pigment Violet 38 (C.I. Vat Violet 3); triarylcarbonium pigments, such as C.I. Pigment Blue 1, 61 and 62; C.I. Pigment Green 1; C.I. Pigment Red 81, 81:1 and 169; C.I. Pigment Violet 1, 2, 3 and 27; C.I. Pigment Black 1 (aniline black); C.I. Pigment Yellow 101 (aldazine yellow), and C.I. Pigment Brown 22.

In one embodiment of the present invention, the organic pigment is selected from the group comprising C.I. Pigment Yellow 138, C.I. Pigment Red 122, C.I. Pigment Violet 19, C.I. Pigment Blue 15:3 and 15:4, C.I. Pigment Black 7, C.I. Pigment Orange 5, 38 and 43 and C.I. Pigment Green 7.

Additionally or alternatively, inorganic pigments can be used.

For example, inorganic pigments like white pigments such as titanium dioxide (C.I. Pigment White 6), zinc white, pigment grade zinc oxide; zinc sulfide, lithopone; lead white; furthermore white fillers such as barium sulfate and $CaCO_3$ which are also referred to as inorganic white pigments in the context of the present invention; black pigments, such as iron oxide black (C.I. Pigment Black 11), iron manganese black, spinel black (C.I. Pigment Black 27), carbon black (C.I. Pigment Black 7); colour pigments, such as chromium oxide, chromium oxide hydrate green; chrome green (C.I. Pigment Green 48); cobalt green (C.I. Pigment Green 50); ultramarine green; cobalt blue (C.I. Pigment Blue 28 und 36); ultramarine blue, iron blue (C.I. Pigment Blue 27), manganese blue, ultramarine violet, cobalt violet, manganese violet, iron oxide read (C.I. Pigment Red 101); cadmium sulfoselenide (C.I. Pigment Red 108); molybdate read (C.I. Pigment Red 104); ultramarine read; iron oxide brown, mixed brown, spinel- and Korundum phases (C.I. Pigment Brown 24, 29 und 31), chrome orange; iron oxide yellow (C.I. Pigment Yellow 42); nickel titanium yellow (C.I. Pigment Yellow 53; C.I. Pigment Yellow 157 und 164); chrome titanium yellow; cadmium sulfide und cadmium zinc sulfide (C.I. Pigment Yellow 37 und 35); Chrome yellow (C.I. Pigment Yellow 34), zinc yellow, alkaline earth metal chromates; Naples yellow; bismuth vanadate (C.I. Pigment Yellow 184); interference pigments, such as metallic effect pigments based on coated metal platelets, pearl luster pigments based on mica platelets coated with metal oxide, and liquid crystal pigments.

In one embodiment of the present invention, the inorganic pigment is selected from the group comprising inorganic yellow pigments, inorganic red pigments and inorganic white pigments. For example, the inorganic pigment is selected from titanium dioxide, barium sulfate and $CaCO_3$.

The term "at least one" pigment means that one or more kinds of pigments can be present in the pigment dispersion. For example, the at least one pigment is a mixture of at least two kinds of pigments, like two or three kinds of pigments.

If the at least one pigment is a mixture of at least two kinds of pigments, it is appreciated that the mixture preferably comprises at least one inorganic pigment.

It is a further requirement of the pigment dispersions according to the present invention, that the pigment dispersion further comprises water or an organic solvent or an inert carrier like a plasticizer. The water can be distilled or fully demineralized water.

If the pigment dispersion according to the invention comprises a plasticizer, the plasticizer is preferably selected from polyglycol, dibasic esters, fatty acids and oils (e.g. mineral oil), fatty esters, phthalates, benzoic esters, DINCH and the like If the pigment dispersion according to the invention comprises an organic solvent, the organic solvent is preferably selected from aromatics like toluene, xylene, alkylbenzenes; acetates like MPA, BuOAc, EtOAc; ketones like MIBK, aceton; aliphatics like paraffine oils, boiling point spirits; ethers likeglycol ethers, butylglycol; and alcohols like texanol, methoxypropanol, butanols. It is appreciated that the organic solvent may be also a mixture of at least two organic solvents.

In one embodiment of the present invention, the inventive pigment dispersion is free of further ingredients. Accordingly, the pigment dispersion consists of
- a) at least one pigment,
- b) the at least one hyperbranched phosphoric acid ester or salt thereof obtainable by the process of the present invention, and
- c) water or an organic solvent or an inert carrier like a plasticizer.

Alternatively, the pigment dispersion according to the invention contains at least one additive (E). For example, the additive (E) may be selected from wetting agents, polyglycols, defoamer and resins different from the hyperbranched phosphoric acid ester or salt thereof, e.g. resins being selected from water soluble alkyd dispersions, water reducible alkyd dispersions, acrylic dispersions, and polyurethane dispersions.

Examples for polyglycols are triethylene glycol, tetraethylenglycol, pentaethylene glycol, polyethylene glycol, for example with an average molecular weight $M_w$ in the range of from 250 to 2,000 g/mol, tripropylene glycol, tetrapropylenglycol, pentapropylene glycol and polypropylene glycol, for example with an average molecular weight $M_w$ in the range of from 300 to 1,000 g/mol, copolymers of ethylene glycol and propylene glycol, in particular block copolymers, and copolymers of ethylene glycol or propylene glycol with 1,2-butylene glycol.

Alkyd dispersions contain at least one water-dispersible or water soluble alkyd resin. Alkyd resins are synthetic polyester resins produced by esterifying polyhydric alcohols, of at least one is trihydric or higher, with polybasic carboxylic acids, and being modified with natural fatty acids or oils and/or synthetic fatty acids, preferably with fatty acids with at least one C—C double bond per molecule. In some embodiments, alkyd resins may be additionally modified with compounds such as resin acids, styrene, benzoic acid, ortho-, meta- or paramethylstyrene, one or more diisocyanates, or one or more compounds selected from acrylic, epoxy, or silicone compounds, see DIN 53183. Suitable diisocyanates for modification are toluene diisocyanate and isophorone diisocyanate.

Examples for acrylic dispersions (also referred to as polyacrylate dispersions or (poly)acrylate binders) are aqueous dispersions that contain at least one poly(meth)acrylate. Poly(meth)acrylates in the context of the present inventions are copolymers of acrylic acid or methacrylic acid or at least one $C_1$-$C_{10}$-alkyl ester of (meth)acrylic acid with at least one comonomer such as vinylaromatic compounds, e.g., styrene, or at least one $C_1$-$C_{10}$-alkyl ester of (meth)acrylic acid, such as methyl acrylate, methyl methacrylate, ethyl acrylate, ethyl methacrylate, n-butyl acrylate, n-butyl methacrylate, 2-ethylhexyl acrylate, or 2-ethylhexyl methacrylate.

Examples for polyurethane dispersions (polyurethane binders) are aqueous dispersions that contain at least one polyurethane with pendent COOH groups or $SO_3^-$-groups, or with polyethyleneglycol units.

Examples for wetting agents are polysilicones and in particular polymers of (meth)acrylic acid or maleic acid, esterified with at least one polyfluorinated alcohol such as $HO$—$(CF_2)_mCF_3$ or $HO$—$CH_2CH_2(CF_2)_mCF_3$, m being a number in the range of from 2 to 20.

With regard to polymers of (meth)acrylic acid or maleic acid, it is appreciated that all carboxylic acid groups or a certain percentage, for example 30 to 90 mole-%, of the carboxylic acid groups may be esterified with polyfluorinated alcohol. The other carboxylic acid groups may be—if applicable—esterified with a non-fluorinated alcohol such as a $C_1$-$C_6$-alkanol, or they may be free acid groups or salts thereof, for example alkali metal salts or ammonium salts, including organic ammonium salts.

For example, maleic acid may be esterified with one or two moles of polyfluorinated alcohol. In case of the respective monoesters, the other carboxylic acid group may be non-esterified, converted into its alkali metal salt, or esterified with a non-fluorinated alcohol such as a $C_1$-$C_6$-alkanol.

Suitable defoamer products include polysiloxane structures carrying alkyl or polyether side chains, which can be used as 100% active materials or dilutions in suitable glyol carriers and optionally containing hydrophobic silica particles. Examples of defoamer that may be used as additive (E) in the pigment dispersion of the present invention are siloxane defoamers such as EFKA®-2580, which is commercially available from BASF SE, Germany.

In one embodiment of the present invention, inventive pigment dispersion comprises from 0.3 to 50% by weight, preferably 1 to 30% by weight, of the hyperbranched phosphoric acid ester or salt thereof, based on the total weight of the at least one pigment in the pigment dispersion.

In one embodiment of the present invention, inventive pigment dispersion comprises from 0.3 to 50% by weight, preferably 1 to 30% by weight, of the hyperbranched phosphoric acid ester or salt thereof, and from 0.1 to 50% by weight of additive (E), preferably 1 to 30% by weight, based on the total weight of the at least one pigment in the pigment dispersion.

In one embodiment of the present invention, the inventive pigment dispersion has solids content in the range of from 1 to 85 wt.-%, preferably 20 to 50 wt.-%, based on the total weight of the pigment dispersion.

The inventive pigment dispersion can be used, e.g., as component in lacquers or paints, for example in water-based lacquers, water-based paints, in solvent-based paints, and in high-solids lacquers (with solids content of 80% or more). They provide lacquers and paints with excellent properties such as good colour reproduction of the pigment, high colour strength, high gloss, acceptable seeding and surface roughness, and—if applicable—alterable shades, in addition to good applicability profiles, high versatility with respect to applications, and good flocculation stability and good rheology. A further aspect of the present invention is thus the use of inventive pigment dispersion as a component in paints or lacquers. A further aspect of the present invention is paints and lacquers, comprising at least one inventive pigment dispersion.

In one embodiment of the present invention, inventive paints contain at least one inventive pigment dispersion and at least one binder, e.g., an acrylic binder or a polyurethane binder.

A further aspect of the present invention is a process for preparing a pigment dispersion according to the present invention, comprising the step of dispersing (A) at least one pigment,
(B) the hyperbranched phosphoric acid ester or salt thereof,
(C) water or an organic solvent or an inert carrier like a plasticizer, and.
(D) at least one Additive (E) selected from wetting agents and polyglycols in a dispersing apparatus.

The at least one pigment (A), hyperbranched phosphoric acid ester or salt thereof (B), water or an organic solvent or an inert carrier like a plasticizer (C) and the at least one additive (E) have been characterized above.

Examples for dispersing apparatuses are mills, such as rotor stator mills, ball mills, bead mills, sand mills, planetary mills, double chamber mills, three roll mills, and stirred ball mills. Further examples for dispersing apparatuses are kneaders, dissolvers, kneader-mixers, planetary kneaders, vat kneaders, and Skandex shakers. Preference is given to ball mills, bead mills, and stirred ball mills.

In one embodiment of the present invention, the dispersing step can be performed at a temperature in the range of from 5 to 80° C.

In one embodiment of the present invention, the dispersing step can be performed over a period of time in the range of from 1 minute to 24 hours, preferably in case of ball mills or stirred ball mills in the range of from 1 to 10 hours, or, in case of three roll mills, 2 to 10 minutes.

It is appreciated that the process for preparing a pigment dispersion according to the present invention may further comprise the formation of a phosphate salt by neutralizing the obtained hyperbranched phosphoric acid ester. Such phosphate salt is preferably formed by contacting the obtained hyperbranched phosphoric acid ester with an inorganic base like alkali hydroxide, e.g. sodium hydroxide and/or potassium hydroxide.

It is appreciated that the formation of such a phosphate salt by neutralizing the obtained hyperbranched phosphoric acid ester is obtained during and/or after the inventive process for preparing a pigment dispersion. For example, the formation of such a phosphate salt is obtained during the inventive process for preparing a pigment dispersion, i.e. during the dispersion of the at least one pigment, the hyperbranched phosphoric acid ester or salt thereof, water or an organic solvent or an inert carrier, and at least one Additive (E) in a dispersing apparatus, preferably the phosphate salt of the hyperbranched phosphoric acid ester is preferably formed in situ.

The scope and interest of the invention will be better understood based on the following examples which are intended to illustrate certain embodiments of the invention and are non-limitative.

EXAMPLES

Example 1

This example illustrates the prior art and concerns the preparation of a hyperbranched polycarbonate as hyperbranched polymer.

The multifunctional alcohol (B3), the diethyl carbonate (A2) and the catalyst (250 ppm based on the total weight of the alcohol) are mixed at room temperature in a 4 L three-necked flask.

Then, the temperature is slowly raised to 140° C. under reflux for two hours. During conversion, ethanol is formed and thus the boiling temperature decreases continuously. When the boiling temperature remains constant, the reflux condenser is then replaced by an inclined condenser, ethanol is distilled off and the temperature is slowly raised to 160° C.

The degree of conversion is estimated by quantifying the amount of separated ethanol. After controlling the molecular weight via GPC (PMMA as reference, DMAc as solvent) the reaction mixture is cooled down, depending on the amount of catalyst, phosphoric acid is added to the reaction mixture, which is then stripped with nitrogen. The analytics of the hyperbranched polycarbonates are set out in Table 1.

The hydroxyl number of the polymers was measured according to DIN 53240. The acid numbers of the polymers were measured according to DIN 53402.

A. Detailed Description of the Synthesis of Polycarbonate PC1

This exemplified description illustrates a detailed preparation procedure of a hyperbranched polycarbonate as hyperbranched polymer.

2400 g Trimethylolpropane x 1,2 Propylenoxid, 1417.5 g Diethylcarbonat and 0.6 g $K_2CO_3$ as catalyst (250 ppm based on the total weight of the alcohol) are mixed at room temperature in a 4 L three-necked flask equipped with stirrer, reflux condenser and internal termomether.

Then, the temperature is slowly raised to 140° C. under reflux for two hours. During conversion, ethanol is formed and thus the boiling temperature decreases continuously. When the boiling temperature remains constant, the reflux condenser is then replaced by an inclined condenser, ethanol is distilled off and the temperature is slowly raised to 160° C.

795 g of Ethanol were collected here.

TABLE 1

| GK Number | Mn (g/mol) | Mw (g/mol) | OH Number | A2 | B3 | Catalyst |
|---|---|---|---|---|---|---|
| PC1 | 820 | 1250 | 416 mgKOH/g | DEC | Trimethylolpropane x 1.2 PO (Propylenoxide) | |
| PC2 | 3200 | 9300 | 238 mgKOH/g | DEC | Glycerin x 5 EO (Ethylenoxide) | |
| PC3 | 2350 | 4716 | 291 mgKOH/g | DEC | Trimethylolpropane x 3 EO (Ethylenoxide) | $K_2CO_3$ |
| PC4 | 3400 | 6400 | 134 mgKOH/g | DEC | Trimethylolpropane x 12 EO (Ethylenoxide) | KOH |
| PC5 | 1800 | 3300 | 206 mgKOH/g | DEC | Trimethylolpropane x 5.4 PO (Propylenoxide) | KOH |

Example 2

This example illustrates the invention and concerns the preparation of a hyperbranched polycarbonate phosphoric acid ester as hyperbranched phosphoric acid ester.

1369.2 g of polycarbonate PC 3 were placed in a 4 L flat flange reactor, equipped with inner thermometer and anchor mixture. The polymer mass was heated at 85° C. under nitrogen atmosphere.

200 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25% (25% of the OH groups of the polycarbonates were reacted to phosphoric acid ester groups).
Mn: 1100 g/mol
Mw: 12900 g/mol
Acid number: 157 mgKOH/g

Example 3

This example illustrates the invention and concerns the preparation of a hyperbranched polycarbonate phosphoric acid ester as hyperbranched phosphoric acid ester.

1369.2 g of polycarbonate PC 3 were placed in a 4 L flat flange reactor, equipped with inner thermometer and anchor mixture. The polymer mass was heated at 85° C. under nitrogen atmosphere.

400 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then the polymer was cooled down up to room temperature.

The analytical details of the obtained hyperbranched phosphoric acid ester were as follows:
Functionalization degree: 50%.
Mn: 620 g/mol
Mw: 830 g/mol
Acid number: 231 mgKOH/g

Example 4

This example illustrates the invention and concerns the preparation of a hyperbranched polycarbonate phosphoric acid ester as hyperbranched phosphoric acid ester.

1374.2 g of polycarbonate PC 1 were placed in 2 L flat flange reactor, equipped with inner thermometer and anchor mixture. The polymer mass was heated at 85° C. under nitrogen atmosphere.

200 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25%.
Mn: 2100 g/mol
Mw: 24400 g/mol
Acid number: 141.56 mgKOH/g

Example 5

This example illustrates the invention and concerns the preparation of a hyperbranched polycarbonate phosphoric acid ester as hyperbranched phosphoric acid ester.

500 g of polycarbonate PC 5 were placed in 4 L flat flange reactor, equipped with inner thermometer and anchor mixture. The polymer mass was heated at 85° C. under nitrogen atmosphere.

103.4 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 50%.
Mn: 1210 g/mol
Mw: 2980 g/mol
Acid number: 165.30 mgKOH/g

Example 6

This example illustrates the prior art and concerns the preparation of a hyperbranched polyether as hyperbranched polymer.

1351 g triethylenglycol (TEG), 1225 g pentaerythritol (PE) and 4 g p-toluene sulfonic acid were placed at room temperature in a 2 L four necked flask, equipped with inner thermometer, stirrer, gas inlet, vacuum connection and distillation bridge. The pressure was reduced to 200 mbar and the reaction mixture was heated to 200° C. 424 g water were distilled out within 10 hours.

The reaction mixture was then neutralized via adding 8 g of a 50% NaOH solution in water. The polymer was then dried under vacuum (300 mbar) for four hours.

Subsequently, the resulting polymer was analyzed via GPC (hexafluoroisopropanol as solvent, PMMA as standard).

The analytical data of the obtained product are reported in Table 2.

TABLE 2

| GK Number | Mn (g/mol) | Mw (g/mol) | OH Number | A2 | B4 | Catalyst |
|---|---|---|---|---|---|---|
| PE1 (GK 3095/13) | 749 | 8670 | 510 mgKOH/g | TEG | PE | p-toluene sulfonic acid |

Example 7

This example illustrates the invention and concerns the preparation of a hyperbranched polyether phosphoric acid ester as hyperbranched phosphoric acid ester.

400 g of polyether PE 1 were placed in 2 L flat flange reactor, equipped with inner thermometer and anchor mixture. The polymer mass was heated at 85° C. under nitrogen atmosphere.

103 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25%.
Acid number: 227.00 mgKOH/g
Mn: 1310 g/mol
Mw: 9790 g/mol Example 8

This example illustrates the prior art and concerns the preparation of a hyperbranched polyether as hyperbranched polymer.

In a 2 L four necked flask, equipped with inner thermometer, stirrer, gas inlet, vacuum connection and distillation bridge, tris-2-hydroxyethylisocyanurate (THEIC) (B3), distilled water, sulphuric acid (93-95% ig) and a di- or multifunctional alcohol (Cn) or a monofunctional alcohol (Dn) were mixed. The reaction mixture was heated at 80° C. under nitrogen stream and stirred for one hour.

The reaction temperature was increased up to 120-130° C. and water was distilled out. After 1 hour the temperature was increased up to 150° C. and the pressure was reduced to 100 mbar. After 40 minutes the reaction was stopped by neutralization of the catalyst by addition of a 50% aqueous solution of NaOH (pH=7). The reaction mixture was then cooled down and analyzed. Gel permeation chromatography was used for determining the molecular weight of the product. As solvent dimethylacetamide (DMAc) was used and as standard for the calibration of the GPC polymethylmethacrylate (PMMA) was chosen.

The OH numbers were measured according to DIN 53240, part 2.

The acid numbers were measured according to DIN 53402.

The analytical data of the obtained product are reported in table 3.

neutralization of the catalyst by adding a 50% aqueous solution of NaOH (pH=7). The reaction mixture was then cooled down and analyzed.

Example 9

This example illustrates the invention and concerns the preparation of a hyperbranched polyether phosphoric acid ester as hyperbranched phosphoric acid ester.

1500 g of polyether PE 2 were placed in 4 L flat flange reactor, equipped with inner thermometer and anchor stirrer. The polymer mass was heated at 85° C. under nitrogen atmosphere.

160.4 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25%.
Mn: 1540 g/mol
Mw: 6240 g/mol
Acid number: 117 mgKOH/g Example 10

This example illustrates the invention and concerns the preparation of a hyperbranched polyether phosphoric acid ester as hyperbranched phosphoric acid ester.

500 g of polyether PE 2 were placed in 2 L flat flange reactor, equipped with inner thermometer and anchor stirrer. The polymer mass was heated at 85° C. under nitrogen atmosphere.

20.1 g of polyphosphoric acid (polyphosphoric acid 115% $H_3PO_4$ equiv) were heated at 80° C. and then were dropped within one hour into the polymer melt by using a drop

TABLE 3

| GK Number | Mn (g/mol) | Mw (g/mol) | OH Number | B3 | Cn (n = 2 or 3) | Dn (n = 1) |
|---|---|---|---|---|---|---|
| PE2 | 1150 | 2914 | 213 mgKOH/g | THEIC | Trimethylolpropane × 12 EO (Ethyleneoxide) | / |
| PE3 | 1038 | 3252 | 268 mgKOH/g | THEIC | Polyethyleneglycol (Pluriol E 200, BASF SE) | / |
| PE4 | 1024 | 3400 | 325 mgKOH/g | THEIC | Trimethylolpropane × 3 EO (Ethyleneoxide) | / |
| PE5 | 1474 | 8209 | 298 mgKOH/g | THEIC | Trimethylolpropane × 12 EO (Ethyleneoxide) | Methylpolyethyleneglykol 500 (Pluriol A 500 E, BASF SE) |

For the synthesis of polyether PE4, 533.0 g THEIC and 1366.8 g trimethylolpropane×12 EO were mixed with 3.0 g sulphuric acid (93-95% ig) as a catalyst and 200.0 g water. The reaction temperature was increased up to 120-130° C. and water was distilled out. After 1 hour the temperature was increased up to 150° C. and the pressure was reduced to 100 mbar. After 40 minutes 716.0 g methylpolyethylene-glykol 500 were added to the reaction mixture.

The temperature was increased up to 150° C. and kept for 4 hours. After 40 minutes the reaction was stopped by funnel. The reaction mixture was then kept for 2 hours at 85° C. Then the polymer was cooled down up to room temperature.

The analytical details of the obtained hyperbranched phosphoric acid ester were as follows:
Functionalization degree: 10%.
Mn: 1870 g/mol
Mw: 5480 g/mol
Acid number: 52 mgKOH/g

Example 11

This example illustrates the invention and concerns the preparation of a hyperbranched polyether phosphoric acid ester as hyperbranched phosphoric acid ester.

1500 g of polyether PE 3 were placed in 4 L flat flange reactor, equipped with inner thermometer and anchor stirrer. The polymer mass was heated at 85° C. under nitrogen atmosphere.

201 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25%.
Mn: 1330 g/mol
Mw: 8030 g/mol
Acid number: 163.17 mgKOH/g

Example 12

This example illustrates the invention and concerns the preparation of a hyperbranched polyether phosphoric acid ester as hyperbranched phosphoric acid ester.

1400 g of polyether PE 4 were placed in 4 L flat flange reactor, equipped with inner thermometer and anchor stirrer. The polymer mass was heated at 85° C. under nitrogen atmosphere.

228 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 25%.
Mn: 1360 g/mol
Mw: 11100 g/mol
Acid number: 141.56 mgKOH/g

Example 13

This example illustrates the invention and concerns the preparation of a hyperbranched polyether phosphoric acid ester as hyperbranched phosphoric acid ester.

500 g of polyether PE 5 were placed in 2 L flat flange reactor, equipped with inner thermometer and anchor stirrer. The polymer mass was heated at 85° C. under nitrogen atmosphere.

30.9 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 10%.
Mn: 1430 g/mol
Mw: 8100 g/mol
Acid number: 82 mgKOH/g

Example 14

This example illustrates the invention and concerns the preparation of a hyperbranched polyether phosphoric acid ester as hyperbranched phosphoric acid ester.

500 g of polyether PE 5 were placed in 2 L flat flange reactor, equipped with inner thermometer and anchor stirrer. The polymer mass was heated at 85° C. under nitrogen atmosphere.

14.9 g of polyphosphoric acid (polyphosphoric acid 115% $H_3PO_4$ equiv) were heated at 80° C. and then were dropped within one hour into the polymer melt by using a drop funnel. The reaction mixture was then kept for 2 hours at 85° C. Then, the polymer was cooled down up to room temperature.

The analytical details of the obtained hyperbranched phosphoric acid ester were as follows:
Functionalization degree: 5%.
Mn: 1450 g/mol
Mw: 5330 g/mol
Acid number: 40 mgKOH/g

Example 15

This example illustrates the prior art and concerns the preparation of linear dispersing agents.

MPEG350-phosphoric ester (comparative 1) used as reference to compare the dispersing efficiency of the transparent iron oxide pigments Sicotrans Yellow L 1916 and Sicotrans Red L 2817. It is prepared according to the following procedure:

232 g of methoxy polyethylene glycol with an average molecular weight of 350 g/mol (Pluriol A 350 E, BASF) is placed in a three necked flask and heated to 30° C. 68.1 g of polyphosphoric acid (polyphosphoric acid 115% $H_3PO_4$ equiv) were heated to 60° C. and then were dropped within one hour into the polyglycol by using a drop funnel. After addition, the reaction mixture was kept at 70° C. for 2 hours until the acid number dropped to 300 mg KOH/g. The slightly yellowish liquid was finally cooled to room temperature and used without further purification.

Example 16

This example illustrates the invention and concerns the testing of a hyperbranched phosphoric acid ester according to the present invention as dispersing agent with regard to its dispersing efficiency for the transparent iron oxide pigments Sicotrans Yellow L 1916 and Sicotrans Red L 2817. In particular, the inventive hyperbranched phosphoric acid ester is tested in comparison to a dispersing agent of the prior art.

The inventive hyperbranched phosphoric acid esters were provided as 100% solid material. For incorporating the inventive hyperbranched phosphoric acid esters into the respective pigment dispersion the samples were first dissolved in water by using a minimum concentration of 20 wt.-%, based on the total weight of the dispersion. The pH of this dispersing agent solution was adjusted with aqueous NaOH to a value of 8-8.5. Depending on the degree of phosphatation of the hyperbranched phosphoric acid ester samples large amounts of NaOH were added to get slightly basic solutions. Dispersions were prepared by mixing the components in the respective addition. The characterization of the pigments and the corresponding dispersant level are outlined in Table 4a below. Furthermore, dispersions were prepared by mixing the components in the respective addition level as outlined in Table 4b below.

TABLE 4a

| Pigment name | CI | BET (m2/g) | Pigment Load | Dispersing agent concentration DOP |
|---|---|---|---|---|
| Sicotrans Yellow L 1916 | PY 42 | 80 | 35% | 15% |
| Sicotrans Yellow L 1916 | PY 42 | 80 | 35% | 30% |
| Sicotrans Red L 2817 | PR 101 | 93 | 35% | 25% |
| Sicotrans Red L 2817 | PR 101 | 93 | 35% | 50% |

TABLE 4b millbase formulations

| Component | Sicotrans Yellow L 1916 | | Sicotrans Red L 2817 | | remark |
|---|---|---|---|---|---|
| Water | 58.45% | 53.2% | 54.95% | 46.2% | |
| Dispersing agent (solid) | 5.25% (15% DOP) | 10.5% (30% DOP) | 8.75% (25% DOP) | 17.5% (50% DOP) | DOP = active dispersant on solid pigment |
| NaOH 10% solution | max 1% | max 1% | max 1% | max 1% | pH adjustment to 8-8.5 |
| Pigment | 35% | 35% | 35% | 35% | Transparent iron oxides |
| EFKA ®-2580 | 0.3% | 0.3% | 0.3% | 0.3% | defoamer |
| Total | 100% Millbase A | 100% Millbase B | 100% Millbase C | 100% Millbase D | |

The obtained dispersions were Skandex shaken for 4 hours at room temperature and the rheology of the obtained millbase was measured after 24 hrs by using a Paar Physika UDS 200 rheometer with a cone/plate geometry. Viscosities were measured in the shear rate ranges from 0.01 to 1024 l/s. For evaluation the viscosities at a shear rate of 1.0 l/s were compared. The viscosity (Brookfield viscosity) is measured in accordance with DIN 53214. Subsequently, 0.3% defoamer (EFKA®-2550), were added to the obtained millbase.

A paint was prepared by mixing part of the obtained millbase (pigment paste) with a modified acrylic water based system. The details regarding the modified acrylic water based system are outlined in Table 5 below.

TABLE 5

| Pos. | Trade name | Function | | w/w % |
|---|---|---|---|---|
| 1. | Neocryl ® XK-98 (45%) | Binder | (1) | 91.20 |
| 2. | Water, deionized | Solvent | — | 4.70 |
| 3. | Diethylene glycolmonoethylether | Solvent | — | 3.40 |
| 4. | Dehydran ® 1293 | Defoamer | (2) | 0.40 |
| 5. | Borchi ®Gel L75 N/water (1/1) | Thickener | (3) | 0.30 |
| | | | | 100.00 |

The positions 1 to 5 as outlined in Table 5 were added and stirred with efficient agitation. Subsequently, 8.6 wt.-% of millbase as outlined in Table 4b was mixed with 91.4 wt.-% of the clear coat, based on the total weight of the obtained pigmented coating. The final pigmented coating (wet) that is applied on the substrate thus contains 3 wt.-% of pigment, based on the total weight of the obtained pigmented coating.

The final pigmented coating was applied to a polyester sheet with a 75μ wire bar coater, and the film was dried overnight at room temperature.

For evaluation coloristic values, the gloss values at a 20°-angle and 60°-angle, the lightness (L*), chroma (C) and hue (h) were measured. For the measurements a Spectrophotometer CM-2600d from Minolta was used and the calculations on the measured values were done with the BASF internal software BSC-Win.

Negative impacts on appearance were seeding, surface roughness and haze. Rating for appearance is: 1=very poor; 2=poor; 3=mediocre; 4=good; 5=excellent.

The Screening results for the pigment pastes and the corresponding dispersing agent added in the composition set out in Table 4 are outlined in the following Tables 6 (for pigment Sicotrans Yellow L 1916) and 7 (for pigment Sicotrans Red L 2817).

TABLE 6

| sample | DOP | Millbase | Gloss @ 20° | Viscosity @ 1 s−1 millbase | Transparency |
|---|---|---|---|---|---|
| Example 15 (comparative) | 15% | A | 59 | 50'400 | 3 |
| | 30% | B | 52 | 61'500 | 1 |
| Example 5 | 15% | A | 54 | 22'200 | 2 |
| | 30% | B | 38 | 138'000 | 1 |
| Example 2 | 15% | A | 67 | 47'200 | 4 |
| | 30% | B | 38 | 317'000 | 1 |
| Example 3 | 15% | A | 44 | 279'000 | 3 |
| | 30% | B | 47 | 328'000 | 1 |
| Example 4 | 15% | A | 73 | 73'900 | 1 |
| | 30% | B | 59 | 81'900 | 3 |
| Example 12 | 15% | A | 60 | 102'000 | 3 |
| | 30% | B | 50 | 196'000 | 1 |
| Example 9 | 15% | A | 73 | 53'800 | 3 |
| | 30% | B | 49 | 96'200 | 2 |
| Example 11 | 15% | A | 66 | 43'800 | 2 |
| | 30% | B | 44 | 107'000 | 1 |

DOP: active dispersant on solid pigment.

It can be gathered from Table 6 that the hyperbranched phosphoric acid ester obtained in accordance with the present invention show clearly improved mechanical and optical properties. In particular, it can be gathered that the hyperbranched phosphoric acid ester obtained in Examples 2 and 11 show clearly improved properties compared to comparative 1 (as prepared in Example 15) at 15% addition level of dispersant on pigment Sicotrans Yellow L 1916 with regard to the film gloss, viscosity and transparency.

TABLE 7

| sample | DOP | Millbase | Gloss @ 20 | Viscosity @ 1 s-1 millbase | Transparency |
|---|---|---|---|---|---|
| Example 15 | 25% | C | 66 | 59'100 | 3 |
| (comparative) | 50% | D | 57 | 36'900 | 3 |
| Example 7 | 25% | C | 53 | 32'500 | 2 |
|  | 50% | D | 52 | 21'000 | 1 |
| Example 9 | 25% | C | 63 | 2'200 | 3 |
|  | 50% | D | 56 | 41'100 | 2 |
| Example 11 | 25% | C | 48 | 2'410 | 1 |
|  | 50% | D | 65 | 33'000 | 3 |

It can be gathered from Table 7 that also hyperbranched phosphoric acid ester obtained in Examples 7, 9 and 11 show significant better viscosities at a comparable gloss and transparency compared to comparative 1 (as prepared in Example 15) at 25% addition level of dispersant on pigment Sicotrans Red L 2817.

Example 17

This example illustrates the invention and concerns the testing of a hyperbranched phosphoric acid ester according to the present invention as dispersing agent in a white opaque coating further comprising a wetting agent.

The wetting agent has been prepared as follows:

A reaction flask with a nitrogen inlet, overhead stirrer and thermometer, was charged with 160 g of sec. butanol, flushed with $N_2$ and heated to 100° C. A premix consisting of 6.5 g of fluorinated monomer ("intermediate B" from U.S. Pat. No. 7,173,084, maleic ester of HO—$CH_2CH_2(CF_2CF_2)_{m.1}CF_2CF_3$, m.1 being selected that the average molecular weight is 443 g/mol), 30.6 g of acrylic acid, 181.4 g of n-butyl acrylate, and 21.8 g of t-butylperoxy-2-ethylhexanoate was added during a period of 4 h to the reaction flask at 100° C. After the addition of the premix, the resulting polymer solution was stirred for 4 h at 100° C. Then, the sec. butanol was distilled off under reduced pressure at 100° C. until a solid content of >98% was reached. The resulting mass was cooled to 60° C. Then 36 g of N,N-dimethyl ethanolamine were added. After homogenization for at 60° C., 124 g of water were added over a period of 30 minutes until a clear solution was obtained. The resulting solution contained (D.3), with a $M_n$ of 1170 g/mol and a polydispersity of 1.6, a solid content of 59.7%, and an acid number of 55 mg KOH/g as a clear light yellow viscous liquid. The solution of (D.3) was used as such, without further purification.

Afterwards, the positions 1 to 3 as outlined in Table 8 below were added to a glass jar in the listed order. Then, an equal weight of the total mass of glass beads with a diameter of 2 mm were added, the mixture was well stirred with a spatula and then ground in a skandex shaker for 2 hours. Afterwards, the glass beads were removed by filtration from the $TiO_2$ paste.

TABLE 8

| Pos. | Trade name | Function | w/w % |
|---|---|---|---|
| 1. | Water, deionized | Solvent | 23.5 |
| 2. | Dispersant (100% delivery form) | Additive | 1.5 |
| 3. | Kronos ® 2310 (Kronos) | $TiO_2$ pigment | 75.0 |
|  |  |  | 100.00 |

The viscosity of the obtained millbase ($TiO_2$ paste) was measured after 24 h with a Paar Physika UDS 200 rheometer having a cone/plate geometry. For evaluation the viscosities at a shear rate of 1.0 l/s were compared. The viscosity (Brookfield viscosity) is measured in accordance with DIN 53214.

A paint was prepared by mixing part of the obtained millbase ($TiO_2$ paste) with a modified acrylic water based system as outlined in Table 9 below.

TABLE 9

| Pos. | Trade name | Function | w/w % |
|---|---|---|---|
| 1. | Neocryl ® XK 90 (DSM Neoresins) | Binder | 82.6 |
| 2 | $TiO_2$ paste (75%) | Pigment concentrate | 16.5 |
| 3. | Wetting agent | Substrate wetting | 0.9 |
|  |  |  | 100.00 |

The positions 1 to 3 as outlined in Table 9 were added and stirred with a spatula for 2 minutes. The final paint was applied to a polyester sheet with a 75μ wire bar coater, and the film was dried overnight at room temperature.

For evaluation the gloss values at an 20°-angle were compared. The gloss values were determined by a Byk-Gardner mirco-TRI-gloss apparatus (Nr. 4430).

Negative impacts on appearance were seeding, surface roughness and haze. Rating for appearance is: 1=very poor; 2=poor; 3=mediocre; 4=good; 5=excellent.

The Screening results for the $TiO_2$ pigment paste and the corresponding dispersing agent added in the composition set out in Table 8 are outlined in the following Table 10.

TABLE 10

| Dispersant Sample used | Acid number mgKOH/g | Viscosity millbase 1/s | Gloss 20 | appearance |
|---|---|---|---|---|
| Example 13 | 82 | 10700 | 56 | 4 |
| Example 14 | 40 | 2650 | 52 | 3 |
| Comparative 1 (Example 15) | 300 | 7220 | 51 | 3 |

From Table 10 it can be gathered that the paint comprising the inventive hyperbranched phosphoric acid ester as dispersing agent (Example 14) shows a significantly improved millbase viscosity compared to the prior art dispersing agent of Example 15 while featuring a comparable gloss and surface quality. It can be further gathered that Example 13 shows a significantly improved gloss and features good film properties.

The invention claimed is:

1. A process for preparing a hyperbranched phosphoric acid ester, the process comprising:
   providing at least one hyperbranched polymer comprising terminal primary hydroxyl groups, secondary hydroxyl groups, or both, wherein the at least one hyperbranched polymer is a polyether, a polyetheramine or a polycarbonate; and
   reacting the at least one hyperbranched polymer directly with at least one phosphoric acid ester-forming compound to obtain a hyperbranched phosphoric acid ester, in which there is no (chain extender) linking chain present or added prior to reacting, between the terminal primary or secondary hydroxyl groups of the at least one hyperbranched polymer and the at least one phosphoric acid ester-forming compound.

2. The process according to claim 1, wherein the at least one hyperbranched polymer is a polycarbonate.

3. The process according to claim 1, wherein the at least one hyperbranched polymer is a polyether.

4. The process according to claim 1, therein the at least one phosphoric acid ester-forming compound is at least one of polyphosphoric acid and $P_2O_5$.

5. The process according to claim 1, wherein an amount of the at least one phosphoric acid ester forming compound is such that a degree of functionalization in the hyperbranched phosphoric acid ester is in the range of from 0.5 to 100%, based on a total amount of the terminal primary hydroxyl groups, the secondary hydroxyl groups, or both, in the at least one hyperbranched polymer.

6. The process according to claim 1, wherein an amount of the at least one phosphoric acid ester forming compound is such that a degree of functionalization in the hyperbranched phosphoric acid ester is in the range of from 0.5 to 50%, based on a total amount of the terminal primary hydroxyl groups, the secondary hydroxyl groups in the polymer, or both, in the at least one hyperbranched polymer.

7. The process according to claim 1, wherein an amount of the at least one phosphoric acid ester forming compound is such that a degree of functionalization of the hyperbranched phosphoric acid ester is in the range of from 0.5 to 25%, based on a total amount of the terminal primary hydroxyl groups, the secondary hydroxyl groups, or both, in the at least one hyperbranched polymer.

8. The process according to claim 1, wherein the reacting occurs at a temperature of from 20 ° C. to 200 ° C.

9. The process according to claim 1, wherein the reacting occurs in an inert atmosphere.

10. The process according to claim 1, further comprising forming a phosphate salt by neutralizing the hyperbranched phosphoric acid ester with an amine or inorganic base.

11. The process according to claim 1, wherein the at least one hyperbranched polymer is a homo-polymer or copolymer of tris-2-hydroxyethylisocyanurate.

12. The process of claim 10, wherein the phosphate salt is formed by neutralizing the hyperbranched phosphoric acid ester with an alkali hydroxide.

13. The process according to claim 1, wherein the at least one hyperbranched polymer is a polyetheramine.

* * * * *